United States Patent
Lucas et al.

(10) Patent No.: US 9,725,539 B2
(45) Date of Patent: *Aug. 8, 2017

(54) DIP-FORMED SYNTHETIC POLYISOPRENE LATEX ARTICLES WITH IMPROVED INTRAPARTICLE AND INTERPARTICLE CROSSLINKS

(71) Applicant: Ansell Healthcare Products LLC, Iselin, NJ (US)

(72) Inventors: David M. Lucas, Melaka (MY); Sugarth Amarasekera, Kotte (LK); Dave Narasimhan, Flemington, NJ (US); Adeline Ai Lin Kung, Petaling Jaya (MY)

(73) Assignee: Ansell Healthcare Products LLC, Iselin, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/725,040

(22) Filed: May 29, 2015

(65) Prior Publication Data

US 2015/0259451 A1    Sep. 17, 2015

Related U.S. Application Data

(63) Continuation of application No. 14/176,608, filed on Feb. 10, 2014, now Pat. No. 9,074,029, which is a
(Continued)

(51) Int. Cl.
*A61F 6/04* (2006.01)
*C08F 136/08* (2006.01)
(Continued)

(52) U.S. Cl.
CPC ........ *C08F 136/08* (2013.01); *A41D 19/0055* (2013.01); *A61F 6/04* (2013.01);
(Continued)

(58) Field of Classification Search
CPC ........ A61L 31/10; A61L 31/06; A61L 29/085; A61L 31/14; A61L 2420/02;
(Continued)

(56) References Cited

U.S. PATENT DOCUMENTS 3,215,649 A    11/1965    Preiss et al.
3,494,781 A    2/1970    Knibbe et al.
(Continued)

FOREIGN PATENT DOCUMENTS

AU    2009241426 B2    11/2009
CN    1479754 A    3/2004
(Continued)

OTHER PUBLICATIONS

Nieuwenhuizen et al., "The Mechanism of Zinc (II)—Dithiocarbamate-Accelerated Vulcanization Uncovered; Theoretical and Experimental Evidence", ACS Publications, J. Am. Chem. Soc. 121(1)—Abstract, Dec. 19, 1998, 1 page.
(Continued)

*Primary Examiner* — Kari Rodriquez
(74) *Attorney, Agent, or Firm* — Moser Taboada

(57) ABSTRACT

A synthetic polyisoprene latex emulsion has pre-vulcanization composition and post vulcanization composition. The pre-vulcanization composition comprises soluble sulfur with high $S_8$ ring structure that is catalytically broken by a zinc dithiocarbamate. Surfactants present in the pre-vulcanization composition wets synthetic polyisoprene particles and permeates small sized sulfur and accelerator molecules into the interior of these particles thereby pre-vulcanizing the particles. The degree of pre-vulcanization is verified by isopropanol index test. The latex emulsion has post-vulcanization composition with accelerators that crosslink interparticle region during post vulcanization cure cycle. The dipped synthetic polyisoprene article is substantially uni-
(Continued)

formly cured both in the inter-particle and intra-particle regions and reliably exhibits high cross link density, uniform distribution of double bonds in TEM and zinc segregation at the boundaries or original particles by electron microprobe analysis. The films exhibit high tensile strength, tensile modulus, tear strength, burst pressure and burst volume.

26 Claims, 7 Drawing Sheets

Related U.S. Application Data continuation of application No. 13/910,364, filed on Jun. 5, 2013, now Pat. No. 9,074,027, which is a continuation of application No. 13/277,445, filed on Oct. 20, 2011, now Pat. No. 8,464,719, which is a continuation of application No. 12/194,118, filed on Aug. 19, 2008, now Pat. No. 8,087,412.

(60) Provisional application No. 61/049,637, filed on May 1, 2008.

(51) Int. Cl.
*A41D 19/00* (2006.01)
*C08L 23/20* (2006.01)
*B32B 27/32* (2006.01)
*B29L 31/48* (2006.01)

(52) U.S. Cl.
CPC ............ *B32B 27/32* (2013.01); *C08L 23/20* (2013.01); *A61F 2006/043* (2013.01); *B29L 2031/4864* (2013.01); *Y10T 428/2982* (2015.01); *Y10T 428/31924* (2015.04)

(58) Field of Classification Search
CPC .. A61L 29/041; A61L 29/14; A61L 2300/404; A61L 29/06; A61L 31/048; A61L 31/141; A61L 2300/102; A61L 2300/104; A61L 27/33; C08L 23/20; C08L 2666/02; C08L 27/18; C08L 83/04; A41D 19/0055; A61F 6/04; A61F 2006/043; A61F 2002/072; A61F 2002/075; A61F 2002/91533; A61F 2002/9155; A61F 2002/91558; A61F 2210/05; C08F 136/08; B29L 2031/4864; B32B 27/32; Y10T 428/2982; Y10T 428/31924
USPC .......................... 128/842, 844; 604/347–353
See application file for complete search history.

(56) References Cited

U.S. PATENT DOCUMENTS

| | | | |
|---|---|---|---|
| 3,897,405 A | 7/1975 | Son et al. | |
| 3,971,746 A | 7/1976 | Hirai et al. | |
| 4,101,481 A | 7/1978 | Branlard et al. | |
| 4,339,372 A | 7/1982 | Branlard et al. | |
| 4,695,609 A | 9/1987 | Stevenson | |
| 4,976,866 A | 12/1990 | Grinstead et al. | |
| 5,149,436 A | 9/1992 | Taniguchi et al. | |
| 5,254,635 A | 10/1993 | Stevenson et al. | |
| 5,322,388 A | 6/1994 | Wells | |
| 5,355,736 A | 10/1994 | Skogley | |
| 5,677,382 A | 10/1997 | Tsuji et al. | |
| 5,744,552 A | 4/1998 | D'Sidocky et al. | |
| 5,773,499 A * | 6/1998 | Umland .................... | C08C 1/06 524/394 |
| 6,112,602 A | 9/2000 | Mitra | |
| 6,114,469 A | 9/2000 | Rauchfuss et al. | |
| 6,221,447 B1 | 4/2001 | Munn et al. | |
| 6,288,181 B1 | 9/2001 | Ford et al. | |
| 6,300,432 B1 | 10/2001 | Ford et al. | |
| 6,313,236 B1 | 11/2001 | Ford et al. | |
| 6,391,326 B1 | 5/2002 | Crepeau et al. | |
| 6,401,547 B1 | 6/2002 | Hatfield et al. | |
| 6,417,296 B2 | 7/2002 | Ford et al. | |
| 6,586,538 B2 | 7/2003 | Ford et al. | |
| 6,618,861 B2 | 9/2003 | Saks et al. | |
| 6,653,380 B2 | 11/2003 | Dzikowicz | |
| 6,673,892 B2 | 1/2004 | Martinez et al. | |
| 6,827,387 B2 | 12/2004 | Kolpasky | |
| 6,828,387 B2 | 12/2004 | Wang et al. | |
| 7,041,746 B2 | 5/2006 | Dzikowicz et al. | |
| 7,048,977 B2 | 5/2006 | Dzikowicz et al. | |
| 7,325,443 B2 | 2/2008 | De Jonge et al. | |
| 7,399,447 B2 | 7/2008 | Bowers et al. | |
| 8,017,680 B2 | 9/2011 | Hill | |
| 8,087,412 B2 * | 1/2012 | Lucas ................ | A41D 19/0055 128/842 |
| 8,464,719 B2 * | 6/2013 | Lucas ................ | A41D 19/0055 128/842 |
| 9,074,027 B2 * | 7/2015 | Lucas ................ | A41D 19/0055 |
| 2003/0161975 A1 | 8/2003 | Lucas et al. | |
| 2004/0071909 A1 | 4/2004 | McGlothlin et al. | |
| 2004/0164456 A1 | 8/2004 | McGlothlin et al. | |
| 2004/0169317 A1 * | 9/2004 | Wang ......................... | C08J 5/02 264/301 |
| 2008/0105064 A1 | 5/2008 | Halland | |
| 2009/0007704 A1 | 1/2009 | Bowers et al. | |
| 2009/0084976 A1 | 4/2009 | Camilli | |
| 2010/0031759 A1 | 2/2010 | Tovena-Pecault | |

FOREIGN PATENT DOCUMENTS

| | | |
|---|---|---|
| CN | 1705687 A | 12/2005 |
| GB | 1111/1914 | 0/1915 |
| GB | 2 088 389 B | 1/1984 |
| GB | 2436566 A | 10/2007 |
| GB | 2436566 A | 10/2007 |
| KR | 101676714 B1 | 11/2016 |
| WO | WO-0177210 A2 | 10/2001 |
| WO | WO-2007113463 A8 | 11/2008 |

OTHER PUBLICATIONS

Nieuwenhuizen "Zinc Accelerator Complexes. Versatile Homogeneous Catalysts in Sulfur Vulcanization", Applied Catalysis A: General, vol. 207, Issue 1-2, pp. 55-68, Feb. 1, 2001.
Burr, "Novel Accelerator Systems for Synthetic Polyisoprene", Waterborne Technologies, R.T. Vanderbilt Company, Inc., Jul. 20, 8 pages, 2004.
Chapman, "Comparison of the Chemistry of Sulphur Vulcanisation of Different Rubbers", Tun Abdul Razak Research Centre, May 16, pp. 1-19, 2006.
Yun et al., "Effect of adding pyridine ligand on the structure and properties of complex Zn(S2CNBz2)2", http://www.chemistrymag.org/cji/2007/097032pe.htm—vol. 9 No. 7, pp. 1-10, Jul. 10, 2007.
Hamed, "Materials and Compounds—Chapter 2", The University of Akron, Akron, Ohio, pp. 11-34, undated, accessed at http://files.hanser.de/hanser/docs/20040401-244515439-6683-3-446-21403-8.pdf on Apr. 22, 2008.
PCT International Search Report and Written Opinion Mailed Jul. 7, 2009 for PCT Application No. PCT/US2009/041756, 5 pages.
International Preliminary Report on Patentability mailed Nov. 11, 2010 for PCT Application No. PCT/US2009/041756, 9 Pages.
Examination Report from the Intellectual Property Office of New Zealand dated Sep. 21, 2011 for Patent Application No. 589447, 1 page.
Extended European Search Report dated Oct. 7, 2011 for Application No. 09739504.0-1214/2280618, PCT/US2009041756, 6 Pages.
Chinese Office Action dated Oct. 8, 2012 for Application No. 200980125646.X, 12 pages.
European Patent Office, Office Action, Application No. 09739504.0-1301, dated May 26, 2014, 5 pages.
C. C. Ho et al., "Surface Morphology of Prevulcanized Natural Rubber Latex Films by Atomic Force Microscopy: New Insight into the Prevulcanization Mechanism," Langmuir 1999, 15, pp. 6208-6219.

(56) References Cited

OTHER PUBLICATIONS

Philippe Henderson, "From Isoprene Monomer to Synthetic Polyisoprene Latex and its Uses," Latex 2001 Conference, Dec. 4-5, 2001, Munich, Germany, pp. 1-24.
Pramuan Tangboriboonrat et al., "Morphology of Natural Rubber Latex Particles Prevulcanized by Sulphur and Peroxide Systems," Colloid Polym Sci (2002) 280; pp. 1097-1103.
K. B. Chakraborty et al., "Technological and Physico-Chemical Behaviour of Safer Accelerators in Synthetic Polyisoprene Latex," Latex 2006, Jan. 24-25, 2006, Frankfurt, Germany, pp. 1-12.
"Preparation of Synthetic Polyisoprene Latex and its use in Coagulant Dipping," Cariflex Polyisoprene Products, 2014 Kraton Performance Polymers, Inc., pp. 1-12.
Aparajita Bhattacharya et al., "Enhanced Process-Effective and Skin-Friendlier Solutions for the Production of Dipped Goods Using Synthetic Polyisoprene-Based Lattices," Cariflex Polyisoprene Products, 2015 Krayton Performance Polymers, Inc., pp. 1-17.
Khalrud B. Chakraborty, et al., "Influence of Accelerators on the Structure, Properties and Processing of Synthetic Polyisoprene Latex," $5^{th}$ International Rubber Glove Conference & Exhibition, pp. 1-5.
R. Russell-Fell, "Compounding and Manufacture of Thin-Wall Latex Products", Latex 2004, Apr. 20-21, 2004, Hamburg, Germany, pp. 95-102.
New Zealand Office Action dated Apr. 12, 2011 for Application No. 589447.
New Zealand Certificate of Grant dated Jul. 9, 2012 for Patent Application No. 589447.
Chinese First Office Action dated Oct. 8, 2012 for Application No. 200980125646.X.
Chinese Second Office Action dated May 6, 2013 for Application No. 200980125646.X.
Japanese First Office Action dated Jun. 25, 2013 for Application No. 2011507552.
Chinese Certificate of Patent for Invention dated Oct. 23, 2013 for Patent No. ZL 200980125646.X.
Japanese Notice of Allowance dated May 1, 2014 for Application No. 2011507552.
European Office Action dated Dec. 4, 2015 for Application No. 09739504.0.
Korean Office Action dated Mar. 16, 2016 for Application No. 10-2010-7026756.
Korean Notice of Allowance dated Mar. 16, 2016 for Application No. 10-2010-7026756.
European Office Action dated Aug. 2, 2016 for Application No. 09739504.0.
Petitioner Expert for Inter Partes Review dated Oct. 10, 2016 for U.S. Pat. No. 9,074,027 B2.
Petitioner Expert for Inter Partes Review dated Oct. 10, 2016 for U.S. Pat. No. 9,074,029 B2.
Petition for Inter Partes Review dated Oct. 12, 2016 for U.S. Pat. No. 9,074,027 B2.
Petition for Inter Partes Review dated Oct. 12, 2016 for U.S. Pat. No. 9,074,029 B2.
European Office Action dated Dec. 2, 2016 for Application No. 09739504.0.
Institution of Inter Partes Review dated Feb. 1, 2017 for U.S. Pat. No. 9,074,027 B2.
Institution of Inter Pules Review dated Feb. 1, 2017 for U.S. Pat. No. 9,074,029 B2.
"IPR2017-00066, U.S. Pat. No. 9,074,029, Patent Owner Response Under 37 C.F.R. §42.120.".
"IPR2017-00063, U.S. Pat. No. 9,074,027, EX2002 to Patent Owner Response (Same Exh. Filed in IPR-2017-0066).".
"IPR2017-00063, U.S. Pat. No. 9,074,027, EX2001 to Patent Owner Response".
"IPR2017-00066, U.S. Pat. No. 9,074,029, Exhibit List for Patent Owner Response".
Declaration of Ho Chee-Cheong, Ph.D. for U.S. Pat. No. 9,074,027 dated Apr. 23, 2017, 31 pgs.
Declaration of Ho Chee-Cheong, Ph.D. for U.S. Pat. No. 9,074,029 dated Apr. 23, 2017, 32 pgs.
*Curriculum Vitae* for Dr. Ho Chee-Cheong.
ISO40742002(E), Natural latex rubber condoms—Requirements and test methods.
Blackley, D. C., "Chapter 17: Latex dipping processes," in *Polymer Latices, Science and technology* 2nd ed. vol. 3, pp. 155-228, London: Chapman & Hall (1997).
Blackley, D. C., "Chapter 8: Investigation of some latex properties," in *Polymer Latices, Science and technology* 2nd ed. vol. 1, pp. 416-540, London: Chapman & Hall (1997).
Ho, C. C. and Khew, H.C., "Low Glass Transition Temperature (Tg) Rubber Latex Film Formation Studied by Atomic Force Microscopy," *Langmuir* 16: 2436-2449 (2000).
Nilsson, Kristian, *Film Formation of Latex in Dry Coating Films*, (Student paper), Karlstads University, 2007.
Ghosh, P., et al., "Sulfur Vulcanization of Natural Rubber for Benzothiazole Accelerated Formulations: From Reaction Mechanisms to a Rational Kinetic Model," *Rubber Chemistry and Technology, Rubber Reviews* 76(3): 592-693 (2003).
Cook, S., et al., "The Microstructure of Natural Rubber Latex Films," *Rubber Chemistry and Technology* 70(4): 549-559 (1997).
Blackley, D. C., "Chapter 1: Introduction" in *Polymer Latices, Science and technology* 2nd ed. vol. 1, pp. 1-31, London: Chapman & Hall (1997).
Paul J. Flory & John Rehner, Jr., "Statistical mechanics of cross-linked polymer networks: II. Swelling," *J. Chem. Phys.* 11(11): 521-526 (1943).
*Encyclopedia of Polymer Science and Technology*, John Wiley & Sons, vol. 7, p. 795, 1967.
Blackley, D. C., "Chapter 13: Chemically-modified latices: 1. Prevulcanized latices," in *Polymer Latices, Science and technology* 2nd ed. vol. 2, pp. 441-511, London: Chapman & Hall (1997).
Hamed, G. R., "Chapter 2: Materials and Compounds" in Engineering with Rubber: How to Design Rubber Components. 2nd ed. Cincinnati: HanserGardner Publications, Inc. (2003).
Ho, C. C. and Khew, M. C., "Surface Morphology of Prevulcanized Natural Rubber Latex Films by Atomic Force Microscopy: New Insight into the Prevulcanization Mechanism," *Langmuir* 15: 6208-6219 (1999).
Second Further Amended Statement of Claim, Apr. 22, 2016.
Second Further Amended Originating Application, Apr. 22, 2016.
Defence to Second Further Amended Statement of claim, Apr. 29, 2016.
Amended Cross-claim and Amended Particulars of Invalidity, Apr. 29, 2016.
Amended Notice of Cross-claim, Apr. 29, 2016.
Defence to Amended Cross-claim, May 6, 2016.
Orders of Rares J, Dec. 19, 2014.
Orders of Rares J, Apr. 10, 2015.
Orders of Rares J, May 22, 2015.
Orders of Rares J, Sep. 25, 2015.
Orders of Rares J, Apr. 15, 2016.
Orders of Rares J, Sep. 28, 2016.
First Affidavit of Dr Ho Chee-Cheong, Jun. 28, 2016.
Annexure HCC-3—Curriculum Vitae of Dr Ho, Jun. 28, 2016.
Annexure HCC-4—List of Dr Ho's selected publications, Jun. 28, 2016.
Second Affidavit of Dr Ho Chee-Cheong, Sep. 23, 2016.
Colour annotated Figure 1 of the Ansell Patent, appearing in paragraph 57 of Dr Ho's second affidavit, Sep. 23, 2016.
Annexure HCC-12—List of documents considered by Dr Ho, Sep. 23, 2016.
First Affidavit of William Duncan Potter, Mar. 3, 2016.
Annexure WDP-1—Dr Potter's curriculum vitae, Mar. 3, 2016.
Annexure WDP-2—Summary of basic matters known in the field as at 2008, Mar. 3, 2016.
Annexure WDP-3—SEM images of natural rubber latex condoms, Mar. 3, 2016.
Third Affidavit of William Duncan Potter, Jun. 29, 2016.
Annexure WDP-6—pp. 448-454 of Blackley text, 1997.

(56) References Cited

OTHER PUBLICATIONS

Annexure WDP-7—article by Ho and Khew dated May 1999.
Fifth Affidavit of William Duncan Potter, Sep. 27, 2016.
Annexure WDP-9—pp. 485-491 of Blackley text, 1997.
Sixth Affidavit of William Duncan Potter, Nov. 4, 2016.
Annexure WDP-10—pp. 216-219 of Blackley text, 1997.
Annexure WDP-11—pp. 277-287 of the Natural Rubber Formulary and Property Index.
Annexure WDP-13—article by Preiss et al. dated 1963.
Annexure WDP-15—article by Cook et al. dated 1997.
Annexure WDP-18—publication by Kraton Polymers dated 2001.
Annexure WDP-19—article by McGlothlin dated 2002.
Annexure WDP-20—article by Burr dated 2004.
Annexure WDP-21—article by Chakraborty and Couchman dated 2006.
Annexure WDP-22—article by Bader dated 2000.
Annexure WDP-23—Dr Potter's handwritten notes of discussion with David Blackley in Feb. 1990 (and typed version thereof).
Annexure WDP-24—emails from Mark McGlothlin to Dr Potter between 1999 to 2000 and email from Peter Philips to David Upstone dated 2000.
Annexure WDP-25—press release by Kraton Polymers dated 2005.
Annexure WDP-26—article by Roland dated 1993.
Annexure WDP-27—set of images reproducing Figure 1 in Ansell Patent using different contrast and brightness, Sep. 27, 2016.
Annexure WDP-28—Dr Potter's notes from ISO working group WG 17 meetings held on Oct. 22, 2001 and Oct. 26, 2001.
Affidavit of Sarah Amelia McKeith, Nov. 15, 2016.
Annexure SAM-1—receipt from purchase of Durex RealFeel condoms made on Jan. 29, 2015.
Annexure SAM-3—receipt from purchase of Durex RealFeel condoms made on Nov. 2, 2016.
Annexure SAM-5—print out of Durex Product webpage, Nov. 15, 2016.
Annexure SAM-6—print out of RB Australia payment portal webpage, Nov. 15, 2016.
First Notice to Admit, Oct. 18, 2016.
Second Notice to Admit, Oct. 19, 2016.
Notice of Dispute in relation to First Notice to Admit, Nov. 1, 2016.
Letter from SSL Australia Pty Ltd to the Therapeutic Goods Administration, Feb. 16, 2012.
Record Summary of ARTG Entry 197226 in the name of Reckitt Benckiser Pty Ltd, May 5, 2012.
Letter from Therapeutic Goods Administration to Reckitt Benckiser Pty Ltd, May 9, 2012.
Annexure WDP-8 to Fifth Potter affidavi—European Patent Office prosecution file for Ansell Healthcare Products LLC's patent application.
Annexure WDP-14 to Sixth Potter affidavit—thesis by Jacqueline Smeaton dated 1998.
Index for Trial Book for *Ansell Healthcare Products LLC & Anor v. Reckitt Benckiser (Australia) Pty. Ltd. ACN 003 274 655 & Ors*, File No. NSD1180/2014 (Federal Court of Australia) Jan. 4, 2017.
Production of Condoms in Accordance with Wang (US 682838762 and US 2004/0169317A1), Apr. 26, 2017, 3 pgs.
Production of Condoms in Accordance with GB566, Apr. 26, 2017, 3 pgs.
Defendant Reckitt Benckiser LLC'S Third Amended Initial Invalidity Contentions, Mar. 20, 2017, 234 pgs.

\* cited by examiner

SEM Micrograph    Zinc Distribution Map    Sulfur Distribution Map

Zinc

SEM Micrograph　　　Zinc Distribution Map　　　Sulfur Distribution Map

Zinc

DIP-FORMED SYNTHETIC POLYISOPRENE LATEX ARTICLES WITH IMPROVED INTRAPARTICLE AND INTERPARTICLE CROSSLINKS

CROSS-REFERENCE TO RELATED APPLICATIONS

This application is a continuation of co-pending U.S. patent application Ser. No. 14/176,608, filed Feb. 10, 2014, now allowed, which is a continuation of U.S. patent application Ser. No. 13/910,364, filed Jun. 5, 2013, now allowed, which is a continuation of U.S. patent application Ser. No. 13/277,445, filed Oct. 20, 2011, which issued as U.S. Pat. No. 8,464,719 on Jun. 18, 2013, which is a continuation of U.S. patent application Ser. No. 12/194,118, filed Aug. 19, 2008, which issued as U.S. Pat. No. 8,087,412 on Jan. 3, 2012, which in turn claims priority to U.S. Patent Application Ser. No. 61/049,637, filed May 1, 2008. The aforementioned related patent applications are herein incorporated by reference in their entireties.

FIELD OF THE INVENTION

The invention relates to producing synthetic polyisoprene articles and method therefor with improved inter particle and intra particle bond using controlled pre-vulcanized particles of synthetic latex that is dip formed into a thin latex article from an aqueous latex emulsion.

BACKGROUND OF THE INVENTION

Condoms and gloves are typically made from vulcanized natural rubber. Natural rubber is produced in latex form by the *Hevea brasiliensis* tree and has unique characteristics. These characteristics make natural rubber particularly useful for the preparation of barrier protection products. Among the unique characteristics of natural rubber is its high level of stereo-regularity, meaning that the polymer of which it is comprised is a chain consisting almost exclusively of cis-1,4 isoprene units. Natural rubber latex is also a highly branched polymer with a high molecular weight and a wide molecular weight distribution. These characteristics of the base latex result in vulcanized rubber film products having a unique combination of strength and elasticity. However, natural polyisoprene also contains proteins that have been shown to produce dermal allergic reaction in some susceptible individuals.

Synthetic polyisoprene has been developed to provide a material with the benefits of natural rubber and to eliminate the potential for protein allergy. However, development of a true replacement for natural rubber has proved to be difficult, with synthetic variants such as that produced by Kraton Inc. by anionic addition polymerization typically has a lower level of stereo-regularity (i.e., less than 90% cis 1,4 isoprene) and reduced molecular weight characteristics. This molecular character, in turn, has resulted in synthetic polyisoprene films having an inferior balance of properties compared to those of vulcanized natural rubber films. Consequently, the addition of a cross-linking agent tends to produce more inter-particle cross-links and less intra-particle cross-links during post-vulcanization, resulting in non-homogeneous cure properties leading to latex film articles having poor strength and elongation properties, such as voids and cracks due to the formation of fractures in the inter-particle regions. In addition, synthetic polyisoprene latex flocks more easily, which result in defects in dipped films, and the latex dip tank has a very limited lifetime that is available for dipping articles. It is, therefore, imperative that synthetic polyisoprene films are cross-linked better to mimic the branched polymeric structure of a natural rubber, thereby providing improved properties.

In dip molding processes, the majority of work with synthetic or natural polyisoprene has been focused on the development of polyisoprene gloves, using a coagulation dip process. In this type of process, a glove-shaped mold is first dipped into a coagulant solution that is known to destabilize the latex formulation. The resulting coagulant layer is then dried, before the mold is dipped into a bath of a compounded latex formulation to form a coagulated wet latex gel. This coagulated wet latex gel is typically leached in water to remove residual surfactant before being dried at a relatively high temperature to complete the cross-linking of the rubber film. The use of a coagulant layer is undesirable in the manufacture of condoms because it impedes the ability to produce a thin latex layer and therefore condoms are dipped over a coagulant free former.

The use of vulcanizing or sulfur cross-linking agents in the manufacture of rubber articles is well-known. The effectiveness of sulfur crosslinking agents is improved by conventional accelerators including dithiocarbamates, thiazoles, guanidines, thioureas, amines, disulfides, thiurams, xanthates and sulfonamides. The use of vulcanizing agents in the manufacture of polyisoprene rubber is disclosed in D'Sidocky et al., U.S. Pat. No. 5,744,552, and Rauchfuss et al., U.S. Pat. No. 6,114,469.

U.S. Pat. No. 3,971,746 to Hirai et al. discloses synthetic polyisoprene rubber latex produced by emulsifying a solution of polyisoprene rubber in an organic solvent including 4-20 wt % of benzene, toluene or xylene with water. After dipping, the solvent is removed by evaporation from the resulting oil-in-water emulsion.

U.S. Pat. No. 4,695,609 to Stevenson discloses vulcanizable rubber compositions containing less than 0.4 parts by weight of nitrosatable materials per 100 parts by weight rubber of xanthogen polysulfide and xanthate compounds. This rubber composition contains a dihydrocarbyl xanthogen polysulphide and a xanthate selected from metal hydrocarbylxanthates and dihydrocarbylxanthates. While commercial aqueous latex compositions are discussed in Examples 9A-E, the aqueous latex compositions do not comprise synthetic polyisoprene. Furthermore, the aqueous latex emulsion 9E contains sulfur, zinc oxide and zinc diethyldithiocarbamate, is stable for only four days, and is capable of producing a product having a tensile strength at fracture of only 22.4 MPa, and an elongation of 830%.

U.S. Pat. No. 5,254,635 to Stevenson discloses a rubber composition containing dibenzylthiuram sulfide. A dibenzylthiuram sulfide, such as tetrabenzylthiuram disulphide, is combined with a dihydrocarbyl xanthogen polysulphide and/or a xanthate to provide a composition, which cross-links natural rubber at 120-180° C. without providing harmful nitrosatables. This natural latex composition, however, is sulfur-free and does not cross-link intra particle regions of a synthetic cis-1,4-polyisoprene having low levels of stereo-regularity. Therefore, the use of this cross-linking agent package for synthetic polyisoprene latex will result in a non-uniform article with inferior properties.

U.S. Pat. No. 6,221,447 to Munn et al. discloses the preparation of hypo-allergenic rubber products, which shrink from a second shape and size to their original shape and size on application of heat. The examples include a polyisoprene condom, which will shrink to fit the individual user during use. The curing package used to make this condom consists of agents such as peroxides and/or sulfur.

U.S. Pat. No. 6,391,326 to Crepeau et al. discloses stable emulsions, methods of preparation, and applications, such as in the formation of elastomeric films. The stable emulsions for preparing an elastomeric film comprise (1) a phase A containing an elastomer dissolved in an organic apolar or slightly polar solvent, in which is dispersed (2) a phase B containing a polymer in solution or dispersed in a polar solvent, which is immiscible with phase A, and (3) a dispersing agent selected from the group consisting of block and grafted polymers. Droplets of phase B having a diameter of 10μ form in phase A. Crepeau et al. does not teach or suggest methods of stabilizing a synthetic polyisoprene latex emulsion against 'flock' formation.

U.S. Pat. No. 6,618,861 to Saks, et al. discloses medical gloves with watch viewing capabilities. This patent discloses a polyisoprene latex compound that includes an accelerator system of 2.0 parts per hundred ("phr") tetramethylthiuram disulfide ("TMTD"), 0.2 phr zinc 2-mercaptobenzothiazole ("ZMBT"), 0.2 phr zinc dibutyldithiocarbamate ("ZDBC"), 0.2 phr 1,3-diphenyl-2-thiourea and 0.2 phr zinc diethyldithiocarbamate ("ZDEC"). However, after curing, this accelerator system provides a product having a tensile strength only of about 1,900 psi.

U.S. Pat. Nos. 6,653,380 and 7,048,977 to Dzikowicz disclose latex film compound with improved tear resistance. The method of enhances the tear resistance, tensile strength, and the aging properties of a latex product by adding an antioxidant synergist with an antioxidant to a latex compound. The latex compound comprises a polymer, a stabilizing system, a film surface conditioner and a curing system that comprises an activator, crosslinker and accelerator. Antioxidant synergists include 2-mercaptobenzimidazole (MBI), 2-mercaptotoluimidazole (MTI), zinc 2-mercaptobenzimidazole (ZMBI) and zinc 2-mercaptotoluimidazole (ZMTI). The latex products formed may be gloves but can also include threads, balloons and other latex-related products. The latex used is not synthetic polyisoprene and the addition of anti-oxidants does not pre-vulcanize the synthetic polyisoprene latex.

U.S. Pat. No. 6,828,387 to Wang et al. discloses polyisoprene articles and a process for making the same. This process produces synthetic polyisoprene articles exhibiting tensile strength properties similar to those of solvent-based processes using natural rubber latex. The process combines a synthetic latex with sulfur, zinc oxide and an accelerator composition comprising a dithiocarbamate, a thiazole, and a guanidine compound, all three of which need to be present, at the pre-cure stage. In a preferred embodiment, the accelerator composition comprises zinc diethyldithiocarbamate (ZDEC), zinc 2-mercaptobenzothiazole (ZMBT), and diphenyl guanidine (DPG), in conjunction with a stabilizer, which is primarily milk protein salt, such as sodium caseinate. Polyisoprene latex (typically 60% solids) and the stabilizer (e.g., sodium caseinate) are combined at ambient temperature (about 20-25° C.). After mixing for a period of time, the mixture is then diluted to 40% solids in water. Wingstay L is then added, and the mixture is stirred for approximately 15 min. At this point, the pH can be adjusted to a range of about 8.5 to 9.0. Zinc oxide is added, followed by the sulfur and accelerator compounds. The elastomeric polyisoprene product made by the process is a surgeon's glove dipped over a coagulant-coated former. The aqueous latex emulsion is stable with a maximum stability of eight days. The tensile strength of the surgical glove product obtained is approximately 3,000 psi (20.6 MPa) (according to ASTM D412).

The accelerators are added to the latex emulsion, but maintained at a low temperature for up to eight days. The dithiocarbamate, a thiazole and a guanidine accelerators must be present in the latex together. The latex stabilizer is sodium casinate. The stability of this aqueous latex composition is better than that of Stevenson (U.S. Pat. No. 4,695,609). The glove formers are dipped in a coagulant solution containing calcium nitrate that is unsuited for coagulant-free dipping of synthetic polyisoprene latex condom.

U.S. Pat. No. 7,041,746 to Dzikowicz discloses accelerator system for synthetic polyisoprene latex. The accelerator system comprises dithiocabamate and thiourea and can produce synthetic polyisoprene films having a tensile strength of about 3,000 psi to about 5,000 psi at low curing temperatures. The accelerator system does not contain tetramethyithiuram disulfide or diphenylguanidine or sodium dibutyldithiocarbamate (SDBC), or diisopropyl xanthogen polysulphide (DXP) but contains thiourea. The accelerators are not indicated to pre-vulcanize the synthetic polyisoprene particles and the latex article produced has a very low modulus of 1.5 MPa at 300% elongation and a tensile strength of 20.6 to 34.4 MPa.

UK patent application GB 2,436,566 to Attrill et al. discloses minimizing pre-vulcanization of polyisoprene latex. This process for making a polyisoprene latex comprises compounding a synthetic polyisoprene latex with compounding ingredients and maturing the latex at a low temperature so as to minimize pre-vulcanization. Dipping of condoms is also conducted at low temperatures typically 15° C. to less than 20° C. The absence of pre-vulcanization is verified be assuring the strength of a ring made has a prevulcanisate relaxed modulus has a value less than 0.1 MPa indicative of the absence of pre-vulcanization. The latex emulsion may contain accelerator such as dithiocarbamate. The '566 patent application teaches away from pre-vulcanization prior to dipping of latex articles.

There is a need, therefore, for a stable synthetic polyisoprene latex emulsion composition that does not agglomerate or flock, providing usable emulsion lifetimes. The composition should achieve substantial intra-particle and inter-particle crosslinking in the final product. Such a composition would enable the dip-forming of articles in the absence of a coagulant, such that articles having thinner, continuous, and defect-free layers with enhanced strength and improved stretchability could be obtained. Such articles would not deteriorate and would maintain their physical integrity over time. It is an object of the present invention to provide such a composition, as well as a method of preparing and using such a composition to dip-form articles, and the articles so produced. These and other objects and advantages, as well as additional inventive features, will become apparent from the detailed description provided herein.

SUMMARY OF THE INVENTION

The present invention provides a latex article that is formed by dipping a condom shaped former in a pre-vulcanized synthetic latex emulsion without use of any coagulants and curing the condom thus produced. Synthetic polyisoprene latex is available from Kraton, which is produced by anionic polymerization with a high cis-1,4 content. The synthetic latex particles in the latex emulsion are pre-vulcanized by the incorporation of sulfur within the interstices of latex particles. This incorporation of sulfur within the synthetic latex particles is accomplished by 1) using a sulfur emulsion that has a high content of soluble sulfur with $S_8$ ring structure; 2) said ring structure being disrupted or broken by catalytic activity of zinc dithiocarbamate resulting in linear sulfur chains in the latex emulsion adapted for easy migration into the particles of synthetic polyisoprene in the latex emulsion; 3) using a potassium caprylate surfactant and sodium dodecyl benzene sulphonate (SDBS) surfactant to wet the particles of synthetic polyisoprene in the latex emulsion there by chains of sulfur along with sulfur captured zinc dithiocarbamate is available for permeation into said particles; 4) allowing sufficient time at selected process temperature in the range of 20° C. to 30° C. to progressively permeate sulfur into said synthetic polyisoprene particles; 5) validating sulfur permeation and pre-vulcanization by isopropanol index test wherein the synthetic polyisoprene particles are no longer very tacky but exhibits lesser degree of tackiness with an isopropanol index of 3. Zinc dithiocabamate is a zinc complex of dithiocarbamate and includes zinc dimethyldithiocarbamate, zinch diethyl dithiocarbamate, zinc dibutyldithiocarbamate. In addition, the synthetic polyisoprene latex emulsion has other crosslinking agents such as sodium dibutyldithiocarbamate (SDBC), tetrabenzyl thiuram disulfide, diisopropyl xanthogen, tetraethylthiuram disulfide, xanthogen sulfide for curing the inter-particle regions during the vulcanization or cure cycle. Insoluble sulfur such as amorphous sulfur or polysulfur present in the sulfur added to the latex emulsion becomes soluble at post-vulcanization cure temperature and reacts with zinc dithiocarbamate accelerator curing inter-particle regions. During post vulcanization cure, pre-vulcanized synthetic polyisoprene particles with the permeated sulfur also cure completely in the intra-particle regions. Therefore using this methodology of using a pre-vulcanization accelerator package and post vulcanization accelerator package a substantially uniform cured synthetic latex condom film is produced.

The product thus produced has several distinguishing features that have imprints of this pre-vulcanization and post-vulcanization methodology. Since the synthetic polyisoprene thin film of latex is cured with improved crosslink density, the molecular weight between crosslinks exhibits a lower value. Since zinc complex of dithiocarbamate catalytically breaks the $S_8$ ring of sulfur and as a catalyst, it is available for subsequent use and does not readily penetrate the synthetic polyisoprene due to its large molecular size. The molecular size of zinc dibutyldithiocarbamate is a larger than that of zinc dimethyldithiocarbamate which has a molecular size greater than that of zinc dimethyldithiocarbamate. Zinc dibenzyldithiocarbamate and zinc diphenyldithiocarbamate are even larger molecules and will resist permeation into the synthetic polyisoprene latex particles. Thus the preferred zinc complex of dithiocarbamate for pre-vulcanization of synthetic latex particles in the latex emulsion is zinc dibutyldithiocarbamate (ZDBC) or zinc diethydithiocarbamate (ZDEC). There is an accumulation of zinc containing compound surrounds each of the original synthetic polyisoprene particles, and this microstructural feature can be readily observed by microprobe elemental analysis using an electron microscope. The synthetic polyisoprene films produced typically have high tensile strength, high tensile modulus and elongation at fracture with the fracture front passing through both the inter particle and intra particle regions indicating that the intra particle regions and inter particle regions are substantially of equal strength within the synthetic latex films produced.

The method for producing synthetic polyisoprene products comprises use of a synthetic latex emulsion that includes a pre-vulcanization composition and post-vulcanization composition along with conventional latex emulsion additives comprising stabilizers, pH control agents, antioxidants, preservatives etc. Preferably, the synthetic polyisoprene particles are cis-1,4-polyisoprene, have a diameter in the range of about 0.2 to 2 micrometers, and are maintained in an aqueous medium of the latex emulsion. Kraton® 'IR-KP401A' latex is supplied by Kraton Polymers Group, 15710 John F. Kennedy Blvd., Suite 300, Houston, Tex. 77032 and has these properties. The pre-vulcanization composition has sulfur with high soluble sulfur content, typically of the $S_8$ ring structure, zinc dithiocarbamate accelerator that can break or disrupt the $S_8$ sulfur ring structure, a combination of surfactants including potassium caprylate also known as potassium salt of octanic acid and sodium dodecyl benzene sulphonate (SDBS). Reference to "high soluble sulfur content" means having enough soluble sulfur present to form sufficient to permeate into latex particles in the aqueous latex emulsion and crosslink during curing to achieve commercially acceptable articles such as condoms and/or gloves. The pre-vulcanization of the synthetic latex particles in the latex emulsion occurs over a period of time between 9 hours to 2 days depending on the temperature of the latex emulsion which is generally in the range of 20° C. to 30° C. The degree of pre-vulcanization of the synthetic latex particles is monitored by an isopropanol index test and the latex particles progress from a very tacky feel (index ~1.0) to a lesser degree of tacky feel (index 3) as pre-vulcanizing sulfur is incorporated within the particle. The post-vulcanization composition includes amorphous or polysulfur, which is insoluble at latex emulsion temperature but is soluble at vulcanization or cure temperature. Other accelerators in the synthetic aqueous latex emulsion includes, but are not limited to zinc diethyldithiocarbamate (ZDEC), to zinc dibutyldithiocarbamate (ZDBC), sodium diethyldithiocarbamate (SDEC), sodium dibutyldithiocarbamate (SDBC), a thiuram compound and diisopropyl xanthogen polysulphide (DXP). Zinc oxide may also be added as an activator.

A typical synthetic polyisoprene latex emulsion composition is provided in terms of 100 parts by weight of dry rubber (phr). The pre-vulcanizing composition includes sulfur in the range of 0.6 to 1.8 wt %; Accelerator package includes ZDEC and/or ZDBC accelerator SDBC accelerator, DXP accelerator together with reactive zinc oxide activator is used with a total accelerator content in the range of 0.6 wt % to 2.5%. The surfactant package includes potassium caprylate, sodium dodecyl benzene sulphonate and polyoxyethylene cetyl/stearyl ether with surfactants in the range of 0.3 to 1.5 wt %; Winsgtay L or butylated reaction product of p-cresol & dicyclopentadiene anti-oxidant preservative is in the range of 0.3 to 1 wt %; ammonium hydroxide is in the range of 0 to 0.36 wt %. As indicated earlier, the pre-vulcanization composition of the synthetic polyisoprene latex composition includes soluble sulfur, ZDEC and/or ZDBC accelerator, potassium caprylate surfactant and SDBS surfactant and polyoxyethylene cetyl/stearyl ether surfactant. The post-vulcanization composition includes sulfur especially that which is insoluble, SDBC accelerator, DXP accelerator, ZDEC and/or ZDBC. The pre-vulcanization composition provides the availability of sulfur to synthetic polyisoprene latex particles in the aqueous synthetic polyisoprene emulsion pre-vulcanizing the intra-particle regions and the entire particle of synthetic polyisoprene is crosslinked during vulcanization cure cycle. The post-vulcanization composition provides the ability to crosslink regions between the particles of synthetic polyisoprene or inter-particle regions thereby assuring a high quality substantially uniformly cured synthetic polyisoprene product.

DETAILED DESCRIPTION OF THE INVENTION

Figure 1:
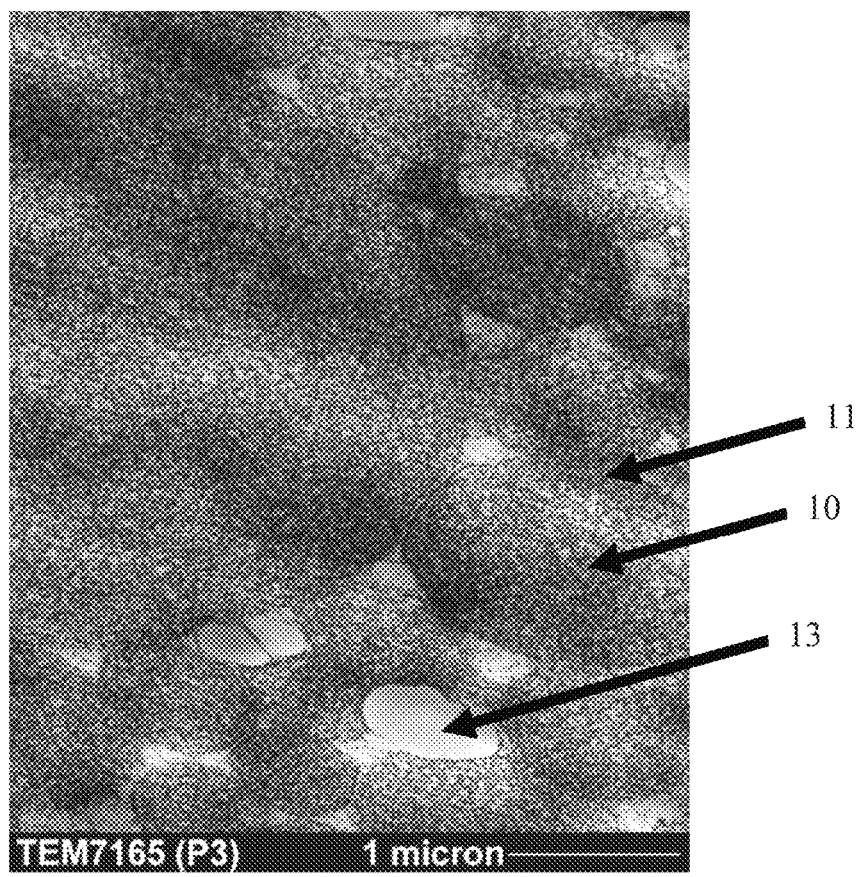
FIG. 1 is a transmission electron micrograph of the middle portion of a pre-vulcanized and post-vulcanized synthetic polyisoprene latex film prepared in accordance with the present invention, wherein 10 shows uniformly distributed, cross-linked networks of polyisoprene particles, 11 shows an inter-particle region, which also evidences uniformly distributed cross-linking, and 13 shows remnants of polystyrene, which is used to swell the film in preparation for the micrograph.
Figure 2:
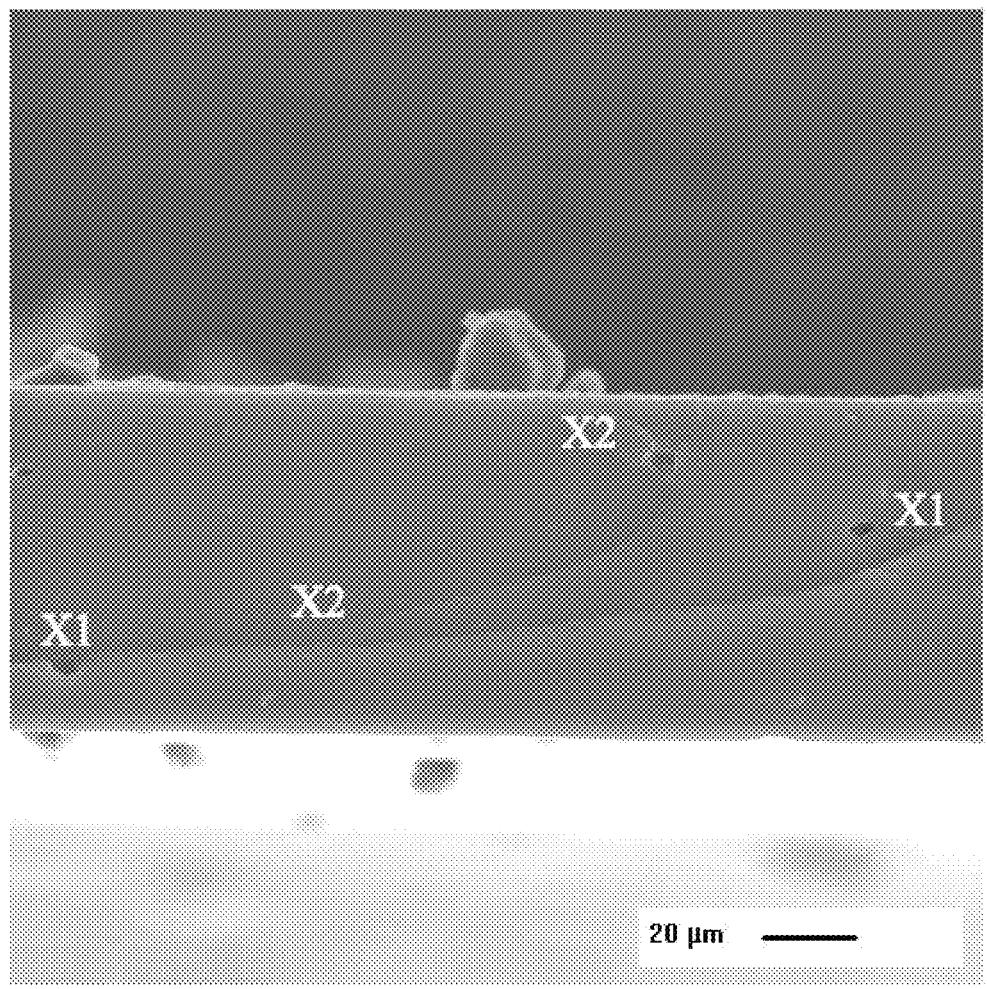
FIG. 2 is a scanning electron micrograph of a cross section of a synthetic polyisoprene condom that was frozen in liquid nitrogen and cleaved. The sample was coated with a thin film of iridium to prevent charging of the insulating latex rubber condom by electron beam. Due to the low temperature of liquid nitrogen, the synthetic polyisoprene condom material behaved as a brittle solid showing conchoidal or shell-like fracture surfaces along X1-X1 and X2-X2. There were no grains visible in this fracture surface, indicating that the fracture strength at the intra grain region and inter grain region was very nearly the same and the therefore the fracture surface was nearly isotropic everywhere. A dimensional marker shows a line, which is calibrated to be 20 microns in length.
Figure 3:
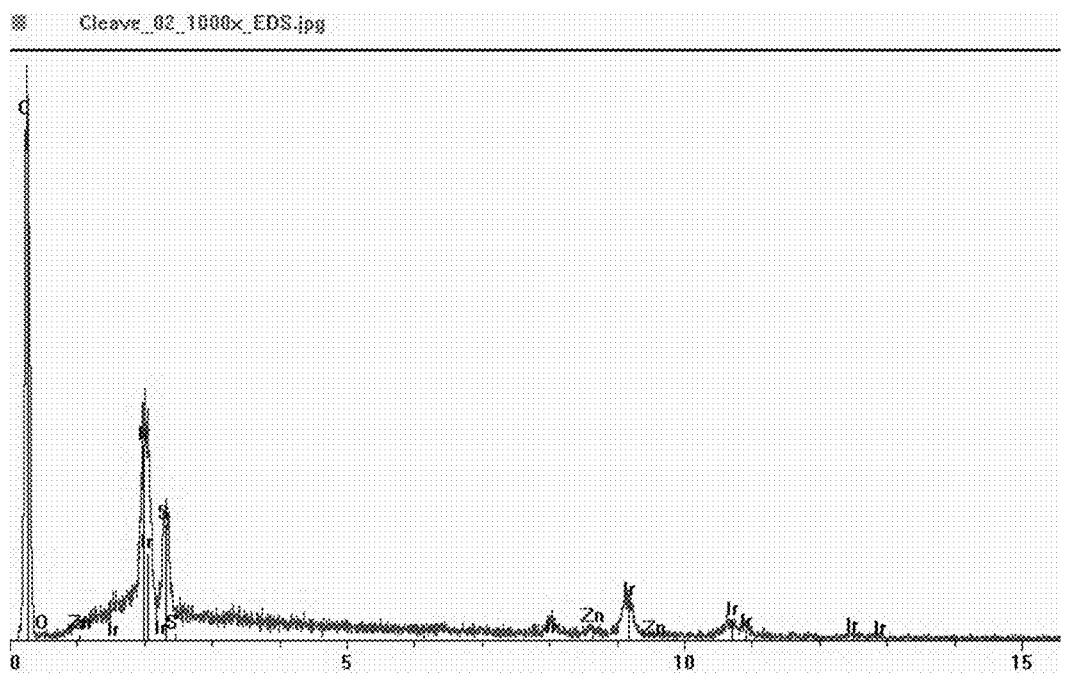
FIG. 3 is an x-ray map of chemical elements present in the sample shown in FIG. 2. It shows one or more x-ray peaks for Zn, S and Ir in addition to carbon.
Figure 4A:
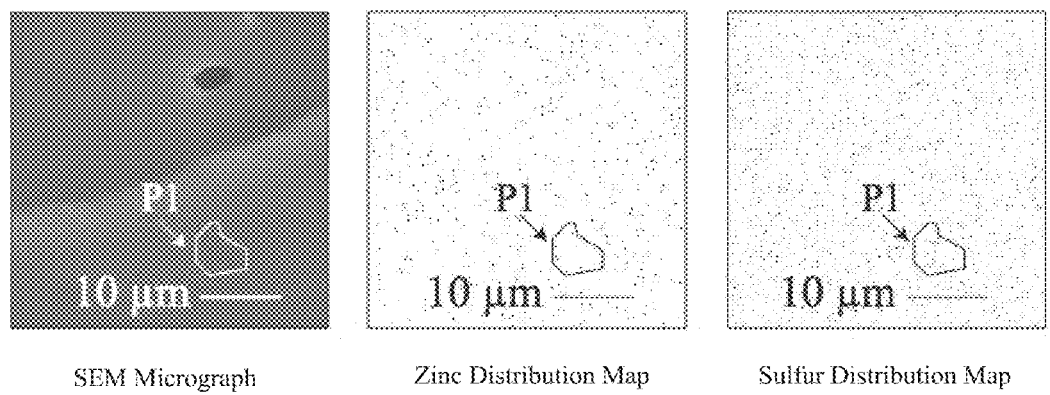
FIG. 4A is a set of three photographic images. A first image provides a scanning electron micrograph of the cross-section show in FIG. 2 at a selected location near the upper marking of X1. An image of a zinc x-ray map in the same area and an image of a sulfur x-ray map are also shown. It is recognized that generally, upon creation, x-ray maps of zinc and sulfur are usually a black background photograph with zinc or sulfur x-ray beams emitted from the sample providing a series of white dots. The zinc map and sulfur map images of FIG. 4A, however, were inverted in contrast for clarity. A selected region marked P1 is shown in all three images. As seen in the zinc x-ray map, the region P1 encompasses a series of zinc black dots that define a region, with no zinc black dots within the region. The corresponding sulfur x-ray map shows plurality of sulfur black dots. From this image, it is concluded that this was a single grain of polyisoprene particle in the polyisorene latex emulsion. It is also concluded that during the pre-vulcanization stage, the sulfur molecule was catalyzed by the ZDBC allowing sulfur to enter the polyisoprene particle, as seen in the sulfur x-ray map. The zinc, on the other hand, was left behind due to the large molecular size of ZDBC decorating the exterior of the polyisoprene particle, as seen in the zinc x-ray map.
Figure 4B:
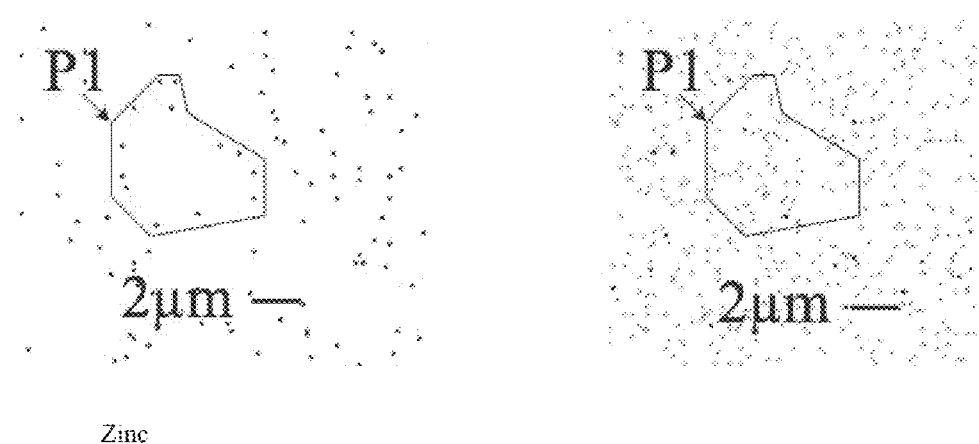
FIG. 4B shows the x-ray maps of zinc and sulfur in the region P1 that have been magnified for clarity, where the zinc black dots and sulfur black dots are clearly visible. The polyisoprene particle in the region P1 has an approximate dimension of 4 microns.
Figure 5:
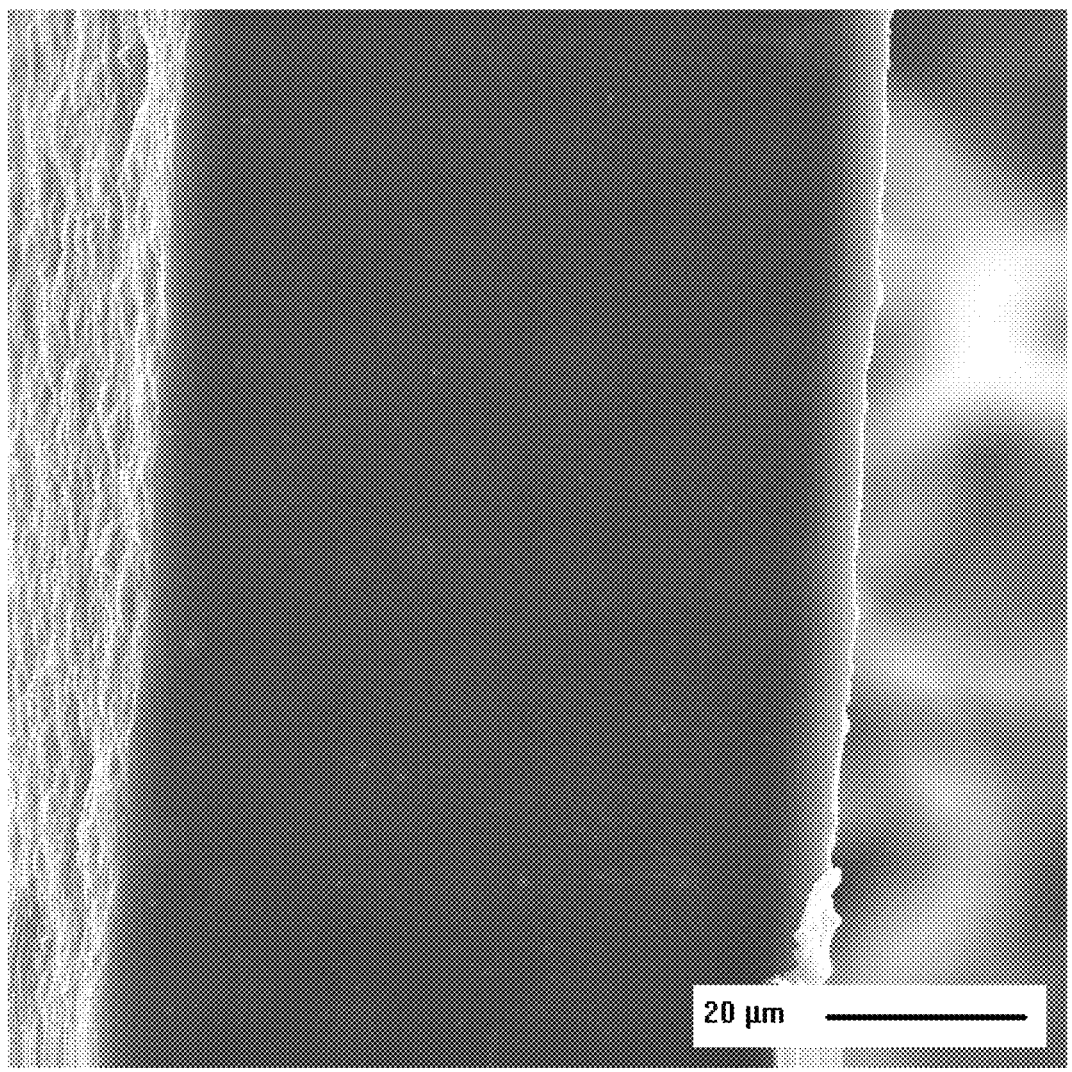
FIG. 5 is a scanning electron micrograph of the fracture surface of a condom that was ruptured by blowing high pressure nitrogen to form a balloon that eventually burst. This test was done at room temperature. The sample was coated with a thin film of iridium to prevent charging of the insulating latex rubber condom by electron beam. The fracture surface as shown in this figure shows a fracture surface that was very nearly planar with no features indicating intra particle or inter particle regions. This absence of intra-polyisoprene particle and inter-polyisooprene particle features means that the fracture surface propagated with no preference for either the intra particle region or the inter particle regions indicating that both inter and intra particle regions were approximately equal strength or were cross-linked nearly equally. The latex condom fractured at room temperature as an elastic solid showing planar fracture surface, not a conchoidal or shell-like fracture surface. There were no grains visible in this fracture surface, indicating that the fracture strength at the intra grain region and inter grain region was very nearly the same and the therefore the fracture surface was nearly isotropic everywhere. A dimensional marker shows a line, which is calibrated to be 20 microns in length.
Figure 6:
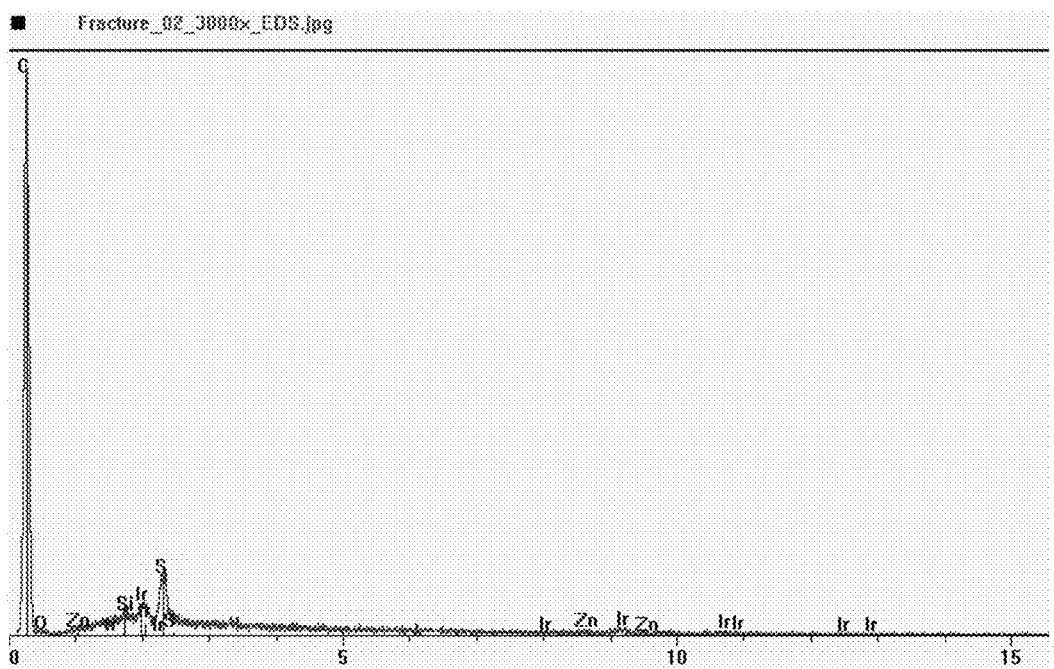
FIG. 6 is an x-ray map of chemical elements present in the sample shown in FIG. 5. It shows one or more x-ray peaks for Zn, S and Ir in addition to carbon.
Figure 7A:
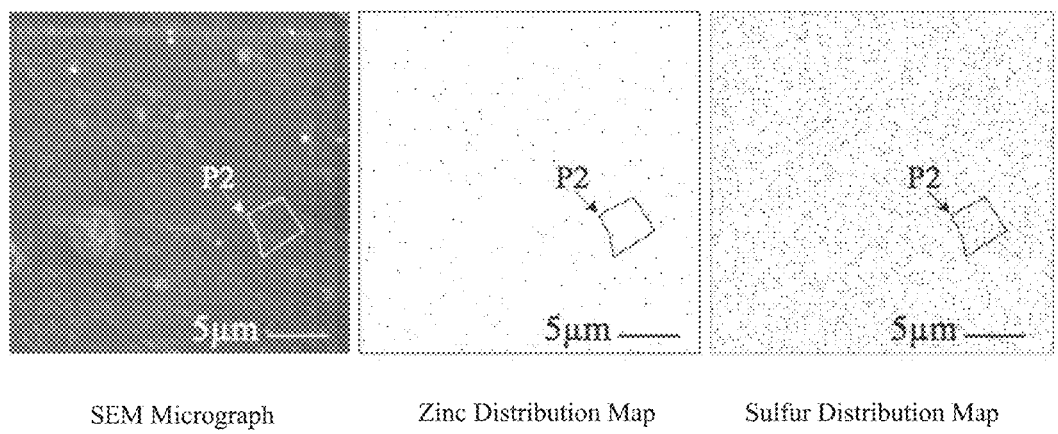
FIG. 7A is a set of three photographic images. A first image provides a scanning electron micrograph of the fracture at a selected location near the circular feature near the central location of FIG. 5. An image of a zinc x-ray map in the same area and an image of a sulfur x-ray map are also shown. It is recognized that generally, upon creation, x-ray maps of zinc and sulfur are usually a black background photograph with zinc or sulfur x-ray beams emitted from the sample providing a series of white dots. The zinc map and sulfur map of FIG. 7A, however, were inverted in contrast for clarity. A selected region marked P2 is shown in all three images. As seen in the zinc x-ray map, the region P2 encompasses a series of zinc black dots that define a region, with no zinc black dots within the region. The corresponding sulfur x-ray map shows plurality of sulfur black dots. From this image, it is concluded that this was a single grain of polyisoprene particle in the polyisorene latex emulsion. It is also concluded that during the pre-vulcanization stage, the sulfur molecule was catalyzed by the ZDBC allowing sulfur to enter the polyisoprene particle, as seen in the sulfur x-ray map. The zinc, on the other hand, was left behind due to the large molecular size of ZDBC decorating the exterior of the polyisoprene particle as seen in the zinc x-ray map.
Figure 7B:
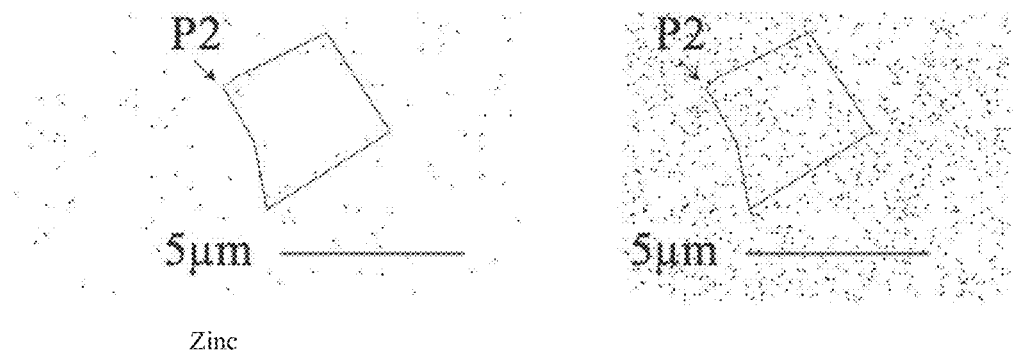
FIG. 7B shows the x-ray maps of zinc and sulfur in the region P2 that have been magnified for clarity, where the zinc black dots and sulfur black dots are clearly visible. The polyisoprene particle in the region P2 has an approximate dimension of 4 microns.

The present invention is predicated on the discovery that soluble sulfur, such as $3_8$ rings of sulfur, is catalyzed by a zinc complex of dithiocarbamate in combination with potassium caprylate and sodium dodecyl benzene sulphonate (SDBS) surfactant creating pre-vulcanized, synthetic polyisoprene particles in a latex composition. This latex composition enables the production of latex film articles by dipping coagulant coated or coagulant free formers into the composition. A surfactant package inhibits synthetic polyisoprene particle agglomeration and flocculation. The latex dipped film has synthetic polyisoprene particles that become crosslinked and regions between the particles are cross-linked during the vulcanization cure forming both intra-crosslinked and inter-crosslinked bonds. The articles that result comprise a high quality and uniform latex film.

The latex-stabilizing composition is one that keeps the particles of synthetic polyisoprene separated from each other in the aqueous medium. Since the polyisoprene particles do not touch each other, they are unable to agglomerate and flock. This is important because, once the particles begin to agglomerate, the particles may never be separated due to van der Waals forces. Preferably, the latex-stabilizing composition comprises a surfactant package comprising at least one surfactant. An anionic surfactant is preferred, especially one that can be stably maintained for a period of well over one month and up to two months or more. An example of such a surfactant is sodium dodecyl benzene sulphonate (SDBS). Other examples include, but are not limited to, other alkyl aryl sulphonates, alkyl sulphonates, olefin sulphonates (e.g., C14 olefin sulphonate, which is sold under the trade name Calsoft AOS-40 (Pilot Chem. Co., Red Bank, N.J.), and alcohol sulphates (e.g., sodium lauryl sulphate). SDBS or another alkyl aryl sulphonate is preferably present in an amount of about 0.1-0.35 wt %, based on the dry weight of the polyisoprene. SDBS or another alkyl aryl sulphonate can be combined with one or more other surfactants, such as potassium caprylate, polyoxyethylene cetyl/stearyl ether, and the like. For example, SDBS or another alkyl aryl sulphonate can be combined with potassium caprylate, alone or in further combination with polyoxyethylene cetyl/stearyl ether. When SDBS or another alkyl aryl sulphonate is used in combination with one or more other surfactants, preferably each surfactant is present in an amount of about 0.05-1.2 wt %, based on the dry weight of the polyisoprene, and the total amount of the surfactant package is about 0.4-1.2 wt %, based on the dry weight of the polyisoprene. When SDBS or another alkyl aryl sulphonate is used in combination with potassium caprylate and polyoxyethylene cetyl-stearyl ether, preferably the polyoxyethylene cetyl-stearyl ether is present in an amount of about 0.1-0.5 wt %, based on the dry weight of the polyisoprene.

In view of the above, the present invention provides a surfactant-stabilized, pre-vulcanized, synthetic polyisoprene latex composition having a isopropanol index rating of 3.0. The isopropanol index test measures the extent of pre-vulcanization of synthetic latex particles in an aqueous latex emulsion by combining equal volumes of latex and isopropanol at room temperature and allowing the mixture to stand for 3 min. The isopropanol coagulates the latex, and the resulting consistency is numerically rated. The consistency of the coagulum indicates the degree of pre-vulcanization of the latex. As the latex becomes more pre-vulcanized, the coagulum loses more of its tackiness and becomes more crumbly. A rating of 2.5 indicates that small lumps form, whereas a rating of 3.0 indicates that the lumps are non-tacky, a rating of 3.5 indicates that, not only are the lumps non-tacky, the lumps disintegrate easily, and a rating of 4.0 indicates that dry crumbs form, evidencing a high degree of pre-vulcanization of the synthetic latex particles. The pre-vulcanization is monitored to assure that the synthetic latex emulsion is ready for dipping of polyisoprene condoms.

The pre-vulcanization composition includes potassium caprylate and SDBS or another alkyl aryl sulphonate surfactants with zinc dithiocarbamate and soluble sulfur. The latex emulsion with surfactants wets the synthetic polyisoprene particles, catalytic action of zinc dithiocarbamate breaks the ring of soluble $S_8$ molecule forming linear chain of soluble sulfur pre-vulcanizing particles of synthetic polyisoprene. The post-vulcanization composition has sulfur and other accelerators that cause inter-particle cross-linking during vulcanization cure. Such cross-linking results in a more homogeneous latex film having greater strength and elongation properties and crosslink density.

Preferably, the pre-vulcanization composition comprises (i) a cross-linking package comprising zinc diethyldithiacarbamate or zinc dibutyldithiocarbamate accelerator and soluble sulfur (ii) a wetting agent. During pre-vulcanization, sulfur with its ring structure broken by the catalytic action of zinc dithiocarbamate accelerator penetrates the polyisoprene particles and initially interacts with the isoprene double bonds therein. The catalytic reactivity of zinc dithiocarbamate is detailed in the publication entitled "The Mechanism of Zinc(II)-Dithiocarbamate-Accelerated Vulcanization Uncovered; Theoretical and Experimental Evidence" by Nieuwenhuizen, et al. is published in J. Am. Chem. Soc., 121 (1), 163-168, 1999. A second publication entitled "Zinc accelerator complexes. Versatile homogeneous catalysts in sulfur vulcanization" by Nieuwenhuizen published in Applied Catalysis A: General 207 (2001) 55-68. These two publications discuss the mechanism of catalytic action of zinc dithiocarbamates specifically zinc dimethyldithiocarbamate with sulfur. The book published by Gary R. Hamed, professor at University of Akron, the chapter 2 of which is available at web address files.hanser.de/hanser/docs/20040401_244515439-6683_3-446-21403-8.pdf clearly indicates in Chapter 2.3.1.1. that for sulfur to be soluble it must have $S_8$ rings. The same chapter indicates that with ZDBC, you need only small amount of sulfur since ZDBC is an ultrafast accelerator. The web article at www.chemistrymag.org/cji/2007/097032pe.htm entitled 'Effect of adding pyridine ligand on the structure and properties of complex $Zn(S_2CNBz_2)_2$,' by Zhong et al. indicates that zinc dibenzyldithiocarbamate and zinc dipyridinedithiocarbamate also have similar functionality of catalytic activity with sulfur.

It is recognized that, unlike the $S_8$ rings of soluble sulfur, amorphous or polymeric sulfur are not soluble. However amorphous or polymeric sulfur becomes soluble at 120° C., which is at or near the latex cure temperature, thus insoluble or polymeric sulfur remain outside synthetic polyisoprene particles in the latex emulsion and facilitates crosslinking of inter particle regions. According to embodiments of the present invention, diffusion of sulfur into synthetic polyisoprene particle requires sulfur to be soluble. The wetting agents used in accordance with the present invention facilitate wetting of the polyisoprene particles and brings soluble sulfur with ring structure broken by zinc dithiocarbamate catalytic action into contact with the surface of the polyisoprene particles and permeation of sulfur occurs during processing time provided. The pre-vulcanized structure of the aqueous latex emulsion is stable for several days, e.g., up to 5 days.

Sulfur is preferably present in the synthetic polyisoprene latex emulsion in an amount of about 0.8-1.8 wt %, based on the dry weight of polyisoprene. If zinc oxide is used, preferably it is present in an amount of about 0-0.5 wt %, based on the dry weight of polyisoprene.

Examples of suitable wetting agents include, but are not limited to, salts (e.g., sodium salt or potassium salt) of fatty acids, which are anionic, e.g., sodium stearate, sodium oleate, and potassium caprylate. Potassium caprylate is advantageously used with a salt of a short-chain fatty acid, SDBS and polyoxyethylene cetyl/stearyl ether.

The penetration of the components of the pre-vulcanizing composition into the polyisoprene particles is a strong function of the polyisoprene particle size and size distribution. Typically, smaller particles have a larger surface area, and the components of the pre-vulcanizing composition penetrate these small particles more rapidly. However, these larger surface areas result in more inter-particle regions, which are cross-linked by the cross-linking agent during post-vulcanization. In contrast, larger particles have a smaller surface area, and the components of the pre-vulcanizing composition penetrate these large particles more slowly. The smaller surface areas result in less inter-particle regions. Aggregates of smaller particles appear like a large particle, which behaves differently than a large particle. Therefore, there is a delicate balance in selecting the size and size range distribution of the polyisoprene particles to produce optimal strength properties that balance pre-vulcanization intra-particle cross-linking with post-vulcanization inter-particle cross-linking. As indicated above, particles in the range of about 0.2-2 micrometers provide optimal results. The penetration of the components of the pre-vulcanizing composition into the polyisoprene particles is also a function of the diffusion process, itself, which is a linear function of time and an exponential function of temperature, reflecting a thermally activated process. Therefore, increasing the temperature by a few degrees during the pre-vulcanization step increases significantly the pre-vulcanization rate. For example, pre-vulcanization at room temperature requires from about 3-5 days or as much as about 9 days, while pre-vulcanization at an elevated temperature, e.g., about 50-70° C., requires only about 3-7 hours.

Preferably, the post-vulcanization composition comprises sodium dibutyl dithiocarbamate (SDBC), sulfur, a thiuram compound, and/or a xanthogen compound, alone or in further combination with a surfactant. Examples of suitable xanthogens include, but are not limited to, diisopropyl xanthogen polysulphide (DXP), diisopropyl xanthogen, tetraethylthiuram disulfide, and xanthogen sulfide. DXP is a preferred xanthogen. An example of a thiuram compound is tetrabenzyl thiuram disulfide. The post-vulcanization composition is one that causes inter-particle cross-linking upon activation at the elevated temperature (e.g., 120-150° C.). In addition, this post-vulcanization cure also crosslinks the synthetic polyisoprene particles with permeated sulfur. Such crosslinking results in a more homogeneous latex film having greater strength and elongation properties.

The method comprises adding a latex-stabilizing composition, such as one comprising a surfactant package comprising at least one surfactant, such as at least one surfactant selected from the group consisting of an alkyl aryl sulphonate (e.g., SDBS), an alkyl sulphonate (e.g., olefin sulphonate) and an alcohol sulphate (e.g., sodium lauryl sulphate). SDBS can be combined with potassium caprylate, alone or with polyoxyethylene cetyl/stearyl ether. A preferred surfactant package comprises SDBS, potassium caprylate, and polyoxyethylene cetyl/stearyl ether. Upon addition of the latex-stabilizing composition, the emulsion is stirred, to keep the polyisoprene particles from touching each other.

Then, the method comprises the steps of adding a pre-vulcanization composition to formulate a synthetic polyisoprene latex emulsion (a) a zinc dithiocarbamate selected from zinc diethyldithiocarbamate and zinc dibutyldithiocarbamate and combinations thereof; (b) sulfur, preferably with high $S_8$ content and (b) a wetting agent. The wetting agent is preferably a salt of a fatty acid, such as sodium stearate, sodium oleate, or potassium caprylate. The aqueous latex emulsion is stirred and periodically examined for permeation of pre-vulcanization agents into the synthetic polyisoprene particles by using the isopropanol index test. The reason why this sequence is adopted is because the polyisoprene latex has an inherent tendency to flock and 'case harden' due to peripheral reaction with sulfur catalyzed by ZDBC or ZDEC. This has to be prevented so that tightly bonded particles do not result. The presence of surfactants and creation of opened out $S_8$ chains of sulfur enables the diffusion of sulfur into the particles.

The method further comprises the steps of adding post-vulcanization composition to the synthetic polyisoprene latex emulsion with accelerators selected from the group consisting of SDBC, reactive zinc oxide, sodium diethyldithiocarbamate, sodium dibutyldithiocarbamate, thiuram such as tetrabenzyl thiuram disulfide and xanthogen. If reactive zinc oxide is present, preferably it is present in an amount of about 0 to 0.5 wt %, based on the dry weight of polyisoprene. The thiuram can be tetraethylthiuram disulfide, tetrabenzyl thiuram disulfide. The xanthogen can be DXP, diisopropyl xanthogen, or xanthogen sulfide. The composition thus produced is stable for up to about 5 days at 20° C. to 25° C. and can be used in a production line.

Table 1 below shows an example of a composition that exhibits pre-vulcanization behavior.

TABLE 1

| Formulation | Quantity per hundred dry rubber (phr) |
|---|---|
| IR-KP 401 Kraton Latex | 100 |
| alkyl aryl sulphonate | 0.1-0.3 |
| potassium caprylate/ potassium oleate | 0.1-0.46 |
| polyoxyethylene cetyl/stearyl ether | 0.1-0.5 |
| sulfur | 0.8-1.8 |
| reactive zinc oxide | 0.05-0.5 |
| ZDEC/ZDBC | 0.4-1.0 |
| SDBC/SDEC | 0.05-0.5 |
| DXP/diisopropyl xanthogen/ xanthogen sulfide | 0.2-0.6 |
| Wingstay L | 0.5-1.0 |

A typical mixing sequence of the aqueous synthetic latex emulsion is illustrated in Table 2. The table lists the steps and the time period involved.

TABLE 2

| Phase I: Addition of chemicals for pre-vulcantion including sulfur, ZDEC/ZDBC, surfactant package with potassium caprylate and polyoxyethylene cetyl/stearyl ether | 5 to 9 days |
|---|---|
| Phase II: addition of post vulcanization accelerators including DXP, SDBC, SDEC, tetrabenzyl thiuram disulfide and surfactants | Prior to dip |

Thus, the present invention further provides a method of forming a synthetic polyisoprene latex article. The method comprises dipping a coagulant-free or coagulant coated former in the above-described pre-vulcanized synthetic polyisoprene aqueous latex emulsion composition at least once to form a thin layer of latex film with individual particles of pre-vulcanized synthetic polyisoprene on the surface of the former. The former can be any suitable former as is known in the art. The present inventive composition is particularly useful for layering onto formers for condoms and gloves.

The method then comprises allowing the thin layer of latex film formed on the surface of the former to dry after each dip. The spaces between the particles decrease as the layer dries. After the last layer of latex film is dry in the case of multiple dips of the former into the synthetic polyisoprene latex emulsion, the method further comprises post-vulcanizing the thin latex film on the former. The film can be post-vulcanized by heating the film, e.g., to about 120 to 150° C. for about 8 to 15 min. During this period, the inter-particle regions are cross-linked. The intra-particle regions also undergo further crosslinking, producing a more homogeneous latex product. Then, the method comprises stripping the latex film from the former.

In the absence of pre-vulcanization of the synthetic polyisoprene particles, crosslinking predominantly occurs in the periphery of the synthetic polyisoprene particles, resulting in weak particles. Attempts to crosslink the intra particle region within the particles only during post-vulcanization results in over crosslinking of the inter-particle regions, which, in turn, results in a latex product with poor stretch properties.

Table 3 lists a typical dipping sequence of a condom. A similar sequence can be created for a synthetic polyisoprene surgical glove.

TABLE 3

First dip (thickness of the film is controlled by total solids content of the latex in the dip tank, the latex viscosity and the speed of the formers).
Drying of the latex film (60-80° C.; 1-3 min).
Second dip (thickness of the film is controlled by total solids content of the latex in the dip tank and the speed of the formers).
Drying of the latex film (60-80° C.; 1-3 min).
Beading/ring formation on the open end of the condom
Drying of the ring and latex film (70-100° C., 1-3 min)
Curing (110-130° C.; 11-15 min)
Leaching (70-80° C., 1-2 min)
Stripping of the condoms from the glass formers The sequence of dipping for the condoms using the surfactant-stabilized, pre-vulcanized synthetic polyisoprene latex composition is typically within the 5-day period, the average lifetime of synthetic polyisoprene latex emulsion tank. A condom former is dipped in the composition in a first dip, and the thickness of the latex film is controlled by the total solids content of the composition in the dip tank and the speed of movement of the formers. The latex film is dried at about 60-80° C. for about 1-3 min. The latex film on the former is dipped again into the composition to apply a second dip coating. The latex film after the second dip is dried at about 60-80° C. for about 1-3 min. The free end of the condom is rolled to create a bead ring and is dried at about 70-100° C. for about 1-3 min. The latex film is post-vulcanized at about 110-130° C. for about 11-15 min. The latex film is leached in water at about 70-80° C. for about 1-2 min to remove residual surfactants and cross-linking agents from the latex film. The latex film is then stripped from the formers. The latex articles produced display higher strength and improved stretch, even when a low stereo-regularity synthetic polyisoprene is used. The synthetic polyisoprene articles are free from irritation-causing proteins and solves the long outstanding problem of latex sensitivity.

Mechanical properties of a synthetic polyisoprene latex film produced according to the subject invention were compared that disclosed in prior art. For example, the synthetic polyisoprene disclosed in U.S. Pat. No. 6,828,387 (Wang) had a tensile strength of over 3000 psi (20.68 MPa), elongation of greater than about 750% at break, and a tensile modulus of less than about 300 psi (2.07 MPa) at 300% elongation as measured in accordance with ASTM D412.

Tensile Properties of synthetic polyisoprene production condom measured according to ISO 4074:2002 test method is shown in the Table 4 below.

TABLE 4

| Batch No. Condom Type | Aged/ Unaged | Tensile Strength MPa | Elongation at Break % | Modulus at 500% MPa |
|---|---|---|---|---|
| 0606030106/ Syn. Polyisoprene | unaged | 35.78 | 1030 | 1.57 |

TABLE 4-continued

| Batch No. Condom Type | Aged/ Unaged | Tensile Strength MPa | Elongation at Break % | Modulus at 500% MPa |
|---|---|---|---|---|
| 0606040116/ Syn. Polyisoprene | unaged | 34.64 | 1022 | 1.38 |
| 0606050116/ Syn. Polyisoprene | unaged | 30.66 | 1017 | 1.38 |
| 0606030106/ Syn. Polyisoprene | 7 days 70° C. | 35.91 | 1033 | 1.39 |
| 0606040116/ Syn. Polyisoprene | 7 days 70° C. | 34.43 | 1021 | 1.39 |
| 0606050116/ Syn. Polyisoprene | 7 days 70° C. | 35.72 | 1050 | 1.44 |
| Natural Rubber | unaged | 29 | 800 | 2 |
| Natural Rubber | 7 days 70° C. | 30 | 800 | 2.1 |

Tear is a very important property of a condom material. Tear strength of synthetic polyisoprene condom was measured and compared with that of natural rubber condom according to ASTM D624: 2000 method and is shown in Table 5 below.

TABLE 5

| Batch No. | Sample Description | Median Tear Strength N/mm | Median Tear Force N | Average Tear Strength N/mm | Average Tear Force N |
|---|---|---|---|---|---|
| 612141816 | Natural Rubber Unaged | 54.26 | 3.62 | 53.29 | 3.57 |
| 612141816 | Natural Rubber Aged 7 days 70° C. | 46.67 | 3.36 | 46.15 | 3.29 |
| 606040116 | Synthetic polyisoprene Unaged | 34.83 | 2.54 | 34.6 | 2.52 |
| 606040116 | Synthetic polyisoprene Aged 7 days 70° C. | 34.13 | 2.33 | 34.65 | 2.37 |

The burst pressure and burst volume of a condom is a critical measure of its performance. Tables 6A and 6B show burst volume and burst pressure data.

TABLE 6A

| | | Burst Unaged (200 pieces tested) | | | | | |
|---|---|---|---|---|---|---|---|
| Condom Type | Condom Batch | MV (L) | SD-V | NCV (pcs) | MP (kPa) | SD-P | NCP (pcs) | Either (pcs) |
| Synthetic PI | 080201PI16 | 53.20 | 3.79 | 0 | 1.70 | 0.13 | 0 | 0 |
| Synthetic PI | 080202PI16 | 54.09 | 4.29 | 0 | 1.72 | 0.15 | 2 | 2 |
| Synthetic PI | 080203PI16 | 50.77 | 3.75 | 0 | 1.81 | 0.15 | 1 | 1 |
| Natural Rubber | 0704150316 | 36.67 | 2.36 | 0 | 2.18 | 0.11 | 0 | 0 |
| Natural Rubber | 0704590316 | 34.40 | 2.39 | 0 | 2.13 | 0.14 | 0 | 0 |

TABLE 6B

| Condom Type | Condom Batch | Burst Aged 7 days 70° C. (200 pieces tested) | | | | | |
|---|---|---|---|---|---|---|---|
| | | MV (L) | SD-V | NCV (pcs) | MP (kPa) | SD-P | NCP (pcs) | Either (pcs) |
| Synthetic PI | 080201PI16 | 46.73 | 3.41 | 0 | 1.57 | 0.12 | 1 | 1 |
| Synthetic PI | 080202PI16 | 49.25 | 3.42 | 0 | 1.54 | 0.12 | 0 | 0 |
| Synthetic PI | 080203PI16 | 47.24 | 4.35 | 0 | 1.51 | 0.14 | 4 | 4 |
| Natural Rubber | 0704150316 | 36.43 | 2.05 | 0 | 2.05 | 0.12 | 0 | 0 |
| Natural Rubber | 0704590316 | 29.30 | 2.88 | 2 | 2.06 | 0.21 | 0 | 2 |

Where MV, P=Mean Volume, Pressure respectively, SD-V, P=Standard Deviation Volume, Pressure respectively, NCV, P=Nonconformance Volume, Pressure respectively The method of measuring molecular weight distribution and calculating crosslink density requires cutting of disks from condom samples and swelling the disk samples in toluene until equilibrium. The disks were initially weighed and after swelling they are weighed again. The equilibrium volume fraction of the swelled rubber $V_r$ was calculated using equation shown below. In this equation $P_r$ is the density of rubber (0.92 g/cm$^3$), $P_s$ is the density of toluene (0.862 g/cm$^3$), $W_r$ is the weight of rubber before swelling and $W_s$ is the weight of swelled rubber.

$$V_r = \frac{\frac{W_r}{P_r}}{\frac{W_r}{P_r} + \frac{W_s - W_r}{P_s}}$$

The volume fraction was used in the Florey-Rehner equation shown below to calculate the crosslink density. In this equation n is the crosslink density, $V_s$ is the molar volume of toluene the swelling solvent, which is 106.3 cm3/mol, $V_r$ is the volume fraction of the rubber phase in the swollen gel, and X is the toluene-cis polyisoprene interaction parameter, which is 0.39.

$$n = \frac{-1}{V_s} \frac{[\ln(1-V_r) + V_r + \chi V_r^2]}{\left[V_r^{\frac{1}{3}} - 0.5 V_r\right]}$$

The molecular weight between crosslinks was calculated by the following equation.

$$M_c = \frac{P_r}{n}$$

Table 7 shown below reports measured molecular weight between crosslinks and corresponding crosslink density for several of synthetic polyisoprene condoms manufactured according the embodiments of the subject invention. Also shown are the values for a synthetic polyisoprene condom marketed by Durex, presumably manufactured according to UK GB 2,436,566 LRC patent application. Also shown are the values for natural rubber condoms. Higher the molecular weight between crosslinks, lower is the crosslink density.

The data presented indicates that the process of the present invention results in synthetic polyisoprene condoms that have very consistent molecular weight between crosslinks. Since Durex polyisoprene condoms have a higher value of molecular weight between crosslinks, the crosslink density is lower than that produced by the present process. The molecular weight between crosslinks for the condoms according to the present invention is comparable to that of natural rubber and has adequate mechanical properties.

TABLE 7

| Condom | Molecular weight between crosslinks (g/mol) | Crosslink Density n mol/cm$^3$ |
|---|---|---|
| Synthetic Polyisoprene Condom Set#1* | 6535 | 0.000141 |
| Synthetic Polyisoprene Condom Set#2* | 6537 | 0.000141 |
| Synthetic Polyisoprene Condom Set#3* | 6754 | 0.000136 |
| Durex Synthetic Polyisoprene condom | 8955 | 0.000103 |
| Natural Rubber regular condom | 5788 | 0.000159 |

*Condoms manufactured according to the subject invention.

FIG. 1 shows a transmission electron micrograph of a pre-vulcanized and post-vulcanized synthetic polyisoprene condom latex taken from the middle portion of the condom thickness. The sample was prepared using the following procedure. Sample regions of the condom sample were taken and extracted in cold acetone overnight to remove any low molecular weight materials that may subsequently interfere with the styrene polymerization process. The samples were then dried for approximately 48 hrs at below 40° C. to remove any solvent traces. The extracted films were then swollen overnight in styrene solution containing 1 wt % benzoyl peroxide initiator and 2 wt % dibutylphthalate plasticizer to aid sectioning. The swollen films were then placed in capsules with excess styrene solution and heated at 70° C. until the styrene had fully polymerized. The styrene-swollen, polymerized samples were sectioned by ultramicrotomy at room temperature. By leaving some polystyrene attached to the surfaces of each condom, it was possible to prepare ultra-thin sections that contained the entire width of each condom. The sections were carefully relaxed by exposure to low levels of xylene vapor and transferred to Transmission Electron Microscopy (TEM) grids. The sections were then stained in osmium tetroxide vapor for one hour and examined by TEM. Osmium tetroxide reacts with carbon-carbon double bonds and, therefore, it imparts a dark stain to polymers containing unsaturated groups, while leaving the polystyrene unstained. The figure shows at 10 the original synthetic polyisoprene particles showing uniform distribution of cross-link networks. The intersection of these particles is shown at 11, and it shows a similar distribution of cross-link networks indicated by uniformity of dark stains, indicating that the synthetic polyisoprene latex film is cross-linked at the synthetic polyisoprene particle level and at intersections. The polystyrene remnants are seen at 13. The overall particle size is approximately 0.8 microns. This homogeneously cured, synthetic polyisoprene results in improved tensile strength at break, superior elongation, and tear properties.

In view of the above, the present invention provides an article made from the above-described surfactant-stabilized, pre-vulcanized, synthetic polyisoprene latex emulsion composition. The article is free from defects and has a stretch to failure of at least about 600%. Table 5 shows an elongation of over 1000% at failure. The article has intra-particle and inter-particle crosslinking and under transmission electron microscopy (TEM) a uniform distribution of dark stains with a deviation of less than about 5% from one location to other within the TEM micrograph. The synthetic polyisoprene article is preferably a condom or a glove.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention, unless otherwise claimed. No language in the specification should be construed as indicating any non-claimed element as essential to the practice of the invention.

What is claimed is:

1. A synthetic polyisoprene elastomeric glove or condom made of a layer of elastomer comprising:
   synthetic polyisoprene particles;
   inter-polyisoprene particle crosslinks; and
   intra-polyisoprene particle crosslinks,
   wherein the glove or condom exhibits a fracture surface with an absence of scanning electron microscope-viewable intra-polyisoprene particle and inter-polyisoprene particle features when ruptured at room temperature.

2. The glove or condom of claim 1, wherein the glove or condom exhibits a substantially conchoidal fracture when fractured at liquid nitrogen temperature.

3. The condom of claim 2, wherein the condom is formed of two or more thin layers of said elastomer consistent with dipping on a former without coagulant on the former.

4. The glove or condom of claim 2, wherein the synthetic polyisoprene particles range in size from about 0.2 to about 2.0 micron.

5. The condom of claim 1, wherein the condom has a tensile strength of at least 30 MPa.

6. The condom of claim 5, wherein the condom exhibits a substantially conchoidal fracture when fractured at liquid nitrogen temperature.

7. The condom of claim 1, wherein the condom is formed of two or more thin layers of said elastomer consistent with dipping on a former without coagulant on the former.

8. The glove or condom of claim 1, wherein said glove or condom exhibits a substantially conchoidal fracture when fractured at liquid nitrogen temperature.

9. The glove or condom of claim 1, wherein the synthetic polyisoprene particles range in size from about 0.2 to about 2.0 microns.

10. The glove or condom of claim 9, wherein the glove or condom exhibits a substantially conchoidal fracture when fractured at liquid nitrogen temperature.

11. A synthetic polyisoprene elastomeric glove or condom made of a layer of elastomer comprising:
    synthetic polyisoprene particles;
    inter-polyisoprene particle crosslinks; and
    intra-polyisoprene particle crosslinks,
    wherein the glove or condom exhibits a substantially conchoidal fracture when fractured at liquid nitrogen temperature.

12. The condom of claim 11, wherein the condom is formed of two or more thin layers of said elastomer consistent with dipping on a former without coagulant on the former.

13. The condom of claim 12, wherein the synthetic polyisoprene particles range in size from about 0.2 to about 2.0 micron.

14. The condom of claim 11, wherein the condom has a tensile strength of at least 30 MPa.

15. The condom of claim 14, wherein the condom has an elongation at break of at least 945%.

16. A synthetic, dip-formed polyisoprene elastomeric condom comprising:
    prevulcanized synthetic polyisoprene particles,
    said synthetic polyisoprene particles bonded to each other through intra-polyisoprene particle crosslinks and inter-polyisoprene particle crosslinks,
    wherein the intra-polyisoprene particle crosslinks and the inter-polyisoprene particle crosslinks are such that the molecular weight is less than about 8400 g/mol between the crosslinks.

17. The condom of claim 16, wherein the condom exhibits a fracture surface with an absence of scanning electron microscope-viewable intra-polyisoprene particle and inter-polyisoprene particle features when ruptured at room temperature.

18. The condom of claim 17, wherein the intra-polyisoprene particle crosslinks and the inter-polyisoprene particle crosslinks are such that the molecular weight is less than about 8000 g/mol between the crosslinks.

19. The condom of claim 18, wherein the condom exhibits a fracture surface with an absence of scanning electron microscope-viewable intra-polyisoprene particle and inter-polyisoprene particle features when ruptured at room temperature.

20. The condom of claim 16, wherein the intra-polyisoprene particle crosslinks and the inter-polyisoprene particle crosslinks are such that the molecular weight is less than about 7500 g/mol between the crosslinks.

21. A synthetic polyisoprene elastomeric condom made of a layer of elastomer comprising:
    synthetic polyisoprene particles;
    inter-polyisoprene particle crosslinks and intra-polyisoprene particle crosslinks, wherein osmium tetroxide staining after styrene swelling, polymerization and sectioning shows distinct, adjacent said particles, and substantially uniformly distributed isoprene double bonds indicative of the intra-polyisoprene particle crosslinks and inter-polyisoprene particle crosslinks being substantially uniformly distributed among and between the synthetic polyisoprene particles.

22. The synthetic polyisoprene elastomeric condom of claim 21, wherein the intra-polyisoprene particle crosslinks and the inter-polyisoprene particle crosslinks are such that the molecular weight is less than about 8400 g/mol between the crosslinks.

23. The synthetic polyisoprene elastomeric condom of claim 21, wherein the intra-polyisoprene particle crosslinks and the inter-polyisoprene particle crosslinks are such that the molecular weight is less than about 8000 g/mol between the crosslinks.

24. The synthetic polyisoprene elastomeric condom of claim 23, wherein the condom has a tensile strength of about 25 Mpa or higher.

25. The synthetic polyisoprene elastomeric condom of claim 21, wherein the intra-polyisoprene particle crosslinks and the inter-polyisoprene particle crosslinks are such that the molecular weight is less than about 7500 g/mol between the crosslinks.

26. The synthetic polyisoprene elastomeric condom of claim 21, wherein the condom has a tensile strength of about 25 Mpa or higher.

* * * * *